United States Patent [19]

Scharwaechter et al.

[11] 4,386,084

[45] May 31, 1983

[54] N-PYRIMIDINYL-CARBAMIC ACID ESTERS, THEIR PREPARATION, AND DRUGS CONTAINING THESE COMPOUNDS

[75] Inventors: Peter Scharwaechter, Moorrege; Klaus Gutsche, Rellingen; Friedrich-Wilhelm Kohlmann, Moorrege; Hinrich Beck, Bad Bramstedt, all of Fed. Rep. of Germany

[73] Assignee: BASF Aktiengesellschaft, Fed. Rep. of Germany

[21] Appl. No.: 322,670

[22] Filed: Nov. 18, 1981

[30] Foreign Application Priority Data

Dec. 4, 1980 [DE] Fed. Rep. of Germany ....... 3045720

[51] Int. Cl.$^3$ ................ C07D 239/49; A61K 31/625; A61K 31/505
[52] U.S. Cl. .................................... 424/229; 424/251; 424/325
[58] Field of Search ................. 544/325; 424/251, 229

[56] References Cited

U.S. PATENT DOCUMENTS

| | | | |
|---|---|---|---|
| 3,919,229 | 11/1975 | Carraz et al. ...................... | 544/325 |
| 4,189,581 | 2/1980 | Scharwaechter et al. .......... | 544/325 |
| 4,279,899 | 7/1981 | Gutsche et al. .................... | 544/325 |
| 4,315,931 | 2/1982 | Scharwaechter et al. .......... | 544/325 |

FOREIGN PATENT DOCUMENTS

850974  5/1977  Belgium .
2709634  9/1978  Fed. Rep. of Germany .

*Primary Examiner*—Mary C. Lee
*Attorney, Agent, or Firm*—Keil & Witherspoon

[57] ABSTRACT

2-Carbamic acid esters of 2,4-diamino-5-(3′,4′,5′-trimethoxybenzyl)-pyrimidine (trimethoprim), a process for their preparation, and drugs containing these compounds, which, as pro-drugs of trimethoprim, have valuable antibacterial properties and potentiate the antibacterial action of sulfonamides.

9 Claims, No Drawings

N-PYRIMIDINYL-CARBAMIC ACID ESTERS, THEIR PREPARATION, AND DRUGS CONTAINING THESE COMPOUNDS

It has been disclosed that substituted 5-benzylpyrimidines are valuable drugs. Thus, for example, 2,4-diamino-5-(3',4',5'-trimethoxybenzyl)-pyrimidine, also called trimethoprim, has been used successfully as an antibacterial compound in human medicine, although it does not always fulfill all the requirements, inter alia because of its relatively short period of action.

Other benzylpyrimidines, for example 4-amido-2-amino-5-(3',4',5'-trimethoxybenzyl)-pyrmidines, have been disclosed in German Laid-Open Application DOS No. 2,709,634 and in Belgian Pat. No. 850,974.

We have found that novel N-pyrimidinylcarbamic acid esters of the formula I

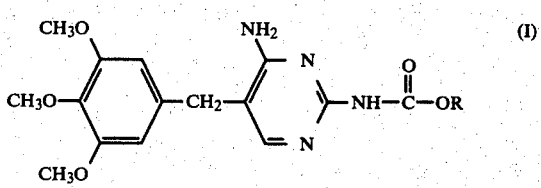

where R is alkyl of 1 to 4 carbon atoms which can be substituted by phenyl, or by alkoxy of 1 to 3 C atoms which is at least 2 carbon atoms removed from the carbamic acid ester oxygen, and their pharmacologically tolerated salts have, as pro-drugs of trimethoprim, valuable antibacterial properties with a longer period of action than trimethoprim, and potentiate the antibacterial action of sulfonamides, by which means an improvement in the overall therapy of bacterial infections can be achieved.

Examples of radicals R are methyl, ethyl, isopropyl, butyl, 2-methoxy-ethyl and benzyl, of which ethyl and 2-methoxy-ethyl are particularly preferred.

The compounds of the formula I according to the invention are prepared by one of the conventional methods of preparing carbamic acid esters, wherein a compound of the formula II

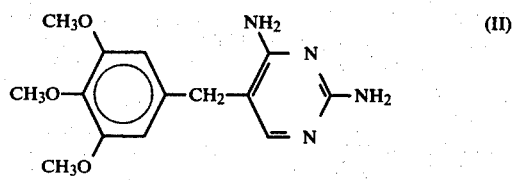

is reacted with a chloroformic acid ester of the formula III

where R has the meanings given in the case of formula I, in the presence or absence of a solvent and in the presence or absence of an acid acceptor.

Advantageous solvents for the reaction are cyclic saturated ethers, such as dioxane or tetrahydrofuran, and aliphatic chlorinated hydrocarbons, such as chloroform. Tetrahydrofuran is particularly preferred. The reaction is preferably carried out at from 0° to 50° C.

Acid acceptors which can be used are tertiary organic bases, for example triethylamine or pyridine, and alkali metal hydroxides, in particular sodium hydroxide. If a tertiary organic base is to be used, an excess may be employed as the solvent. Acid addition salts, and especially salts which can be used in pharmaceutical products, are prepared using the acids usually employed for this purpose, that is to say inorganic acids such as hydrochloric acid, sulfuric acid, phosphoric acid and the like, or organic acids such as formic acid, acetic acid, lactic acid and the like. Other suitable acids are mentioned, for example, in J. Pharm. Sci., 66 (1977), 1–5.

The compounds of the formula I according to the invention and their salts have an antibacterial action and, when combined with antibacterial sulfonamides, potentiate the actions of these compounds. Examples of such sulfonamides are sulfadiazine, sulfamethoxine, sulfadimethoxine, sulfamethoxazole, sulfamoxole, 5-sulfa-3,4-dimethyl-isoxazole and 4-sulfanilamido-5,6-dimethoxypyrimidine. They can therefore be used, for example, to treat bacterial infections of the respiratory organs, digestive organs and urinary tract, ear, nose and throat infections and systemic infectious diseases in general.

The ratio of the compounds of the formula I to the above sulfonamides in the combinations can vary from 1:5 to 5:1, preferably from 1:5 to 1:1. 20 to 500 mg of an active compound of the formula I are in general used as a single dose.

Accordingly, the present invention also relates to a pharmaceutical formulation or a chemotherapeutic agent containing a compound of the formula I, or a pharmacologically tolerated salt thereof, as claimed in claim 1, with or without antibacterial sulfonamide, as well as non-toxic, therapeutically tolerated solid or liquid carriers and pharmaceutical auxiliaries, and to the use of the compounds of the formula I as sulfonamide potentiators.

The pharmaceutical agents and formulations are prepared in a conventional manner, the active compounds being mixed with the conventional non-toxic, therapeutically tolerated solid or liquid carriers and with the conventional pharmaceutical auxiliaries (cf. L. G. Goodman and A. Gilman, The Pharmacological Basis of Therapeutics).

The preferred formulations are those suitable for oral administration. Examples of these are tablets, film tablets, coated tablets, capsules, pills, powders, solutions and suspensions.

To demonstrate the prolonged antibacterial activity, Sprague-Dawley rats weighing about 200 g were treated once, orally, with 40 mg/kg of trimethoprim or with an equimolar amount of the substance to be tested, and were exsanguinated by cardiocentesis after 1, 3, 5 or 7 hours. The content of active compound in the serum was determined in an agar diffusion test, using *Bacillus pumilus* as the indicator organism (S. R. M. Bushley and G. H. Hitchings, Brit. J. Pharmacol. Chemother. 33 (1968), 72–90), and the concentration was determined, with the aid of the inhibiting areolas of trimethoprim standards produced under the same experimental conditions, both graphically (P. Klein, Bakteriologische Grundlagen der chemotherap. Laboratoriumspraxis, Springer-Verlag) and by calculation (J. V. Bennett et al., Appl. Microbiol. 14 (1966), 170–177) and was compared with that of trimethoprim.

Table 1 shows the results of these investigations. It is found that, in the case of the substances from Examples 1 and 2, the retention time of microbiologically active material in the serum is up to three times longer than in the case of trimethoprim (TMP).

TABLE 1

Antibacterial material in the serum of rats after administration of 40 mg/kg of trimethoprim (TMP) or of the equimolar amount of the compound from Example 1 or 2

| Example | Serum level (μg of TMP/ml) ... hours after administration | | | |
|---|---|---|---|---|
| | 1 | 3 | 5 | 7 |
| 1 | 1.89 | 1.75 | 1.34 | 0.54 |
| 2 | 2.0 | 1.23 | 0.62 | 0.33 |
| TMP | 6.34 | 2.5 | 0.72 | 0.18 |

The Examples which follow illustrate the present invention.

EXAMPLE 1

3.81 ml of ethyl chloroformate, dissolved in 20 ml of tetrahydrofuran, are added dropwise to a suspension of 11.6 g of 2,4-diamino-5-(3',4',5'-trimethoxybenzyl)-pyrimidine (trimethoprim) in 80 ml of tetrahydrofuran and 5.56 ml of triethylamine at from 3° to 5° C., with stirring. After the mixture has been stirred at room temperature for 10 hours, the precipitate is separated off, washed with water and dissolved in dimethylformamide. Water is added to the dimethylformamide solution to give 12.1 g (84.1% of theory) of crystalline ethyl N-[4-amino-5-(3',4',5'-trimethoxybenzyl)]-pyrimidin-2-yl-carbamate of melting point 205°–208° C.

$C_{17}H_{22}N_4O_5$ (362.38): calculated: C: 56.34%; H: 6.12%; N: 15.46%. found: C: 56.2%; H: 6.2%; N: 15.3%.

EXAMPLE 2

3.62 g of ethyl N-[4-amino-5-(3',4',5'-trimethoxybenzyl)]-pyrimidin-2-yl-carbamate are dissolved in 75 ml of chloroform at the boiling point, and 30 ml of a saturated diisopropyl ether/hydrogen chloride solution are added dropwise, with stirring. After trituration of the oily precipitate with diisopropyl ether, 3.1 g of crystalline ethyl N-[4-amino-5-(3',4',5'-trimethoxybenzyl)]-pyrimidin-2-yl-carbamate hydrochloride of melting point 170° C. (decomposition) are obtained.

$C_{17}H_{23}ClN_4O_5$ (398.86): calculated: C: 51.19%; H: 5.81%; N: 14.05%; Cl: 8.89%. found: C: 50.9%; H: 5.85%; N: 14.5%; N: 8.6%.

The following compounds are synthesized by a method similar to that in Example 1:

EXAMPLE 3

Methyl N-[4-amino-5-(3',4',5'-trimethoxybenzyl)]-pyrimidin-2-yl-carbamate of melting point 200° C. is synthesized from methyl chloroformate and 2,4-diamino-5-(3',4',5'-trimethoxybenzyl)-pyrimidine.

$C_{16}H_{20}N_4O_5$ (348.35): calculated: C: 55.16%; H: 5.79%; N: 16.08%. found: C: 54.9%; H: 5.8%; N: 16.0%.

EXAMPLE 4

2-Methoxy-ethyl N-[4-amino-5-(3',4',5'-trimethoxybenzyl)]-pyrimidin-2-yl-carbamate of melting point 211°–215° C. is synthesized from 2-methoxy-ethyl chloroformate and 2,4-diamino-5-(3',4',5'-trimethoxybenzyl)-pyrimidine.

$C_{18}H_{24}N_4O_6$ (392.4): calculated: C: 55.09%; H: 6.17%; N: 14.28%. found: C: 54.6%; H: 6.2%; N: 14.3%.

EXAMPLE 5

Isopropyl N-[4-amino-5-(3',4',5'-trimethoxybenzyl)]-pyrimidin-2-yl-carbamate of melting point 192°–195° C. is synthesized from isopropyl chloroformate and 2,4-diamino-5-(3',4',5'-trimethoxybenzyl)-pyrimidine.

$C_{18}H_{24}N_4O_5$ (376.4) calculated: C: 57.43%; H: 6.43%; N: 14.89%. found: C: 56.9%; H: 6.3%; N: 14.8%.

EXAMPLE 6

Butyl N-[4-amino-5-(3',4',5'-trimethoxybenzyl)]-pyrimidin-2-yl-carbamate of melting point 206° C. is synthesized from butyl chloroformate and 2,4-diamino-5-(3',4',5'-trimethoxybenzyl)-pyrimidine.

$C_{19}H_{26}N_4O_5$ (390.43): calculated: C: 58.45%; H: 6.71%; N: 14.35%. found: C: 57.9%; H: 6.7%; N: 14.4%.

EXAMPLE 7

Isobutyl N-[4-amino-5-(3',4',5'-trimethoxybenzyl)]-pyrimidin-2-yl-carbamate of melting point 198° C. is synthesized from isobutyl chloroformate and 2,4-diamino-5-(3',4',5'-trimethoxybenzyl)-pyrimidine.

$C_{19}H_{26}N_4O_5$ (390.43): calculated: C: 58.45%; H: 6.71%; N: 14.35%. found: C: 57.9%; H: 6.74%; N: 14.54%.

EXAMPLE 8

Benzyl N-[4-amino-5-(3',4',5'-trimethoxybenzyl)]-pyrimidin-2-yl-carbamate of melting point 240° C. is synthesized from benzyl chloroformate and 2,4-diamino-5-(3',4',5'-trimethoxybenzyl)-pyrimidine.

$C_{22}H_{24}N_4O_5$ (424.44): calculated: C: 62.25%; H: 5.70%; N: 13.20%. found: C: 61.8%; H: 5.7%; N: 12.3%.

Examples of formulations

EXAMPLE 9

400 mg of 2-sulfanilamido-5-methoxy-pyrimidine (sulfamethoxydiazine)
80 mg of ethyl N-[4-amino-5-(3',4',5'-trimethoxybenzyl)]-pyrimidin-2-yl-carbamate
20 mg of corn starch
10 mg of gelatin
8 mg of talc
2 mg of magnesium stearate
20 mg of Primojel The active compounds and corn starch are mixed and granulated with aqueous gelatin solution. The dry granules are sieved and mixed with the additives. The mixture is tableted in a conventional manner.

EXAMPLE 10

250 mg of 2-sulfanilamido-5-methoxy-pyrimidine (sulfamethoxydiazine)
100 mg of ethyl N-[4-amino-5-(3',4',5'-trimethoxybenzyl)]-pyrimidin-2-yl-carbamate
5 mg of gelatin
30 mg of corn starch
4 mg of talc
1 mg of magnesium stearate The active compounds are granulated with aqueous gelatin solution, and the granules are dried and mixed with the corn starch, talc and magnesium stearate. This mixture is tableted in a conventional manner.

EXAMPLE 11

400 mg of 2-sulfanilamidopyrimidine (sulfadiazine)
80 mg of ethyl N-[4-amino-5-(3',4',5'-trimethoxybenzyl)]-pyrimidin-2-yl-carbamate
20 mg of corn starch
10 mg of gelatin
8 mg of talc
2 mg of magnesium stearate
20 mg of Primojel The active compounds and corn starch are mixed, and granulated with aqueous gelatin solution. The dry granules are sieved and mixed with the additives. This mixture is tableted in a conventional manner.

EXAMPLE 12

250 mg of 2-sulfanilamido-pyrimidine (sulfadiazine)
100 mg of ethyl N-[4-amino-5-(3',4',5'-trimethoxybenzyl)]-pyrimidin-2-yl-carbamate
1.9 g of tylose C 30
30.0 g of sugar
10.0 g of glycerol
2.5 g of bentonite
0.06 g of flavoring
0.04 g of Nipagin M
0.06 g of sodium Nipasol
demineralized water to 100.000 g.

The very finely ground active compounds are suspended in the aqueous tylose mucilage. All the other constituents are added in succession, with stirring. Finally, the mixture is made up to 100.0 g with water.

We claim:
1. An N-pyrimidinyl-carbamic acid ester of the general formula I

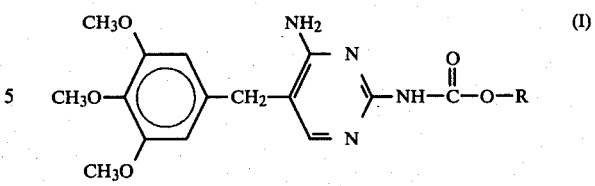

where R is alkyl of 1 to 4 carbon atoms which can be substituted by phenyl, or by alkoxy of 1 to 3 C atoms which is at least 2 carbon atoms removed from the carbamic acid ester oxygen, and pharmacologically tolerated salts thereof.

2. Ethyl N-[4-amino-5-(3',4',5'-trimethoxybenzyl)]-pyrimidin-2-yl-carbamate and its pharmacologically tolerated salts.

3. (2-Methoxy)-ethyl N-[4-amino-5-(3',4',5'-trimethoxybenzyl)]-pyrimidin-2-yl-carbamate and its pharmacologically tolerated salts.

4. Benzyl N-[4-amino-5-(3',4',5'-trimethoxybenzyl)]-pyrimidin-2-yl-carbamate and its pharmacologically tolerated salts.

5. An anbibacterial pharmaceutical formulation which comprises: an effective amount of a compound of the formula I as defined in claim 1, or a pharmacologically tolerated salt thereof, and a non-toxic, therapeutically tolerated solid or liquid carrier.

6. A pharmaceutical formulation as set forth in claim 5, which contains an antibacterial sulfonamide in a ratio of a compound of the formula I to sulfonamide of from 1:5 to 5:1.

7. A pharmaceutical formulation as set forth in claim 6 wherein the ratio of the compound of the formula I to sulfonamide is from 1:5 to 1:1.

8. An antibacterial pharmaceutical formulation in dosage form containing from 20 to 500 mg of a compound of the formula I as defined in claim 1, or a pharmacologically tolerated salt thereof, and a non-toxic, therapeutically tolerated solid or liquid carrier.

9. An antibacterial pharmaceutical formulation in dosage form containing an antibacterial sulfonamide and from 20 to 500 mg of a compound of the formula I as defined in claim 1, or a pharmacologically tolerated salt thereof, said formulation further including a non-toxic, therapeutically tolerated solid or liquid carrier.

* * * * *